United States Patent [19]

Hargis

[11] Patent Number: 4,950,799

[45] Date of Patent: Aug. 21, 1990

[54] PROCESS FOR CATALYTIC REDUCTION OF CARBOXYLIC ACIDS TO ALDEHYDES

[75] Inventor: Duane C. Hargis, Baton Rouge, La.

[73] Assignee: Ethyl Corporation, Richmond, Va.

[21] Appl. No.: 351,925

[22] Filed: May 15, 1989

[51] Int. Cl.$^5$ .................. C07C 45/00; C07C 45/41
[52] U.S. Cl. ........................ 568/484; 568/435
[58] Field of Search ...................... 568/435, 484

[56] References Cited

U.S. PATENT DOCUMENTS

| | | | |
|---|---|---|---|
| 2,033,539 | 3/1936 | Ralston et al. | 568/484 |
| 3,517,066 | 6/1970 | Gurien et al. | 568/435 |
| 3,978,140 | 8/1976 | Lane et al. | 568/435 |
| 4,093,661 | 5/1982 | Trecker et al. | 568/435 |
| 4,328,373 | 5/1982 | Strojny | 568/435 |
| 4,585,899 | 4/1986 | Gelbein et al. | 568/435 |
| 4,585,900 | 4/1986 | Holy et al. | 568/435 |
| 4,605,782 | 8/1986 | John | 568/484 |
| 4,613,700 | 9/1986 | Maki et al. | 568/435 |
| 4,663,479 | 5/1987 | Velenyi et al. | 568/484 |

FOREIGN PATENT DOCUMENTS 0046128  2/1982  European Pat. Off. ............ 568/484

OTHER PUBLICATIONS

Chemical Abstracts, vol. 73, p. 308 (1970), Abstract 14170z.
Chemical Abstracts, vol. 74, p. 429 (1971) Abstract 125138e.
Chemical Abstracts, vol. 78, p. 380 (1973) Abstract 159179x.
Chemical Abstracts, vol. 80, p. 320 (1974) Abstract 59470h.
Chemical Abstracts, vol. 80, p. 351 (1974) Abstract 119810f.
Chemical Abstracts, vol. 82, p. 335 (1975) Abstract 116749y.
Chemical Abstracts, vol. 86, p. 563 (1977) Abstract 171496w.
Chemical Abstracts, vol. 89, p. 619 (1978) Abstract 23937n.
Chemical Abstracts, vol. 91, p. 93 (1979) Abstract 41152y.
Chemical Abstracts, vol. 94, p. 531 (1981) Abstract 30336x.
Chemical Abstracts, vol. 95, p. 617 (1981) Abstract 6491u.
Chemical Abstracts, vol. 96, p. 703 (1982) Abstract 217449v.
Chemical Abstracts, vol. 99, p. 562 (1983) Abstract 139539v.
Chemical Abstracts, vol. 105, p. 132 (1986) Abstract 45253n.
Chemical Abstracts, vol. 106, p. 435 (1987) Abstract 4655x.
Chemical Abstracts, vol. 106, pp. 561-562 (1987) Abstract 18102b.
Chemical Abstracts, vol. 107, p. 103 (1987) Abstract 25141n.

Primary Examiner—Werren B. Lone
Attorney, Agent, or Firm—John F. Sieberth; Terry B. Morris

[57] ABSTRACT

Monocarboxylic acids or esters thereof are reduced to aldehydes using hydrogen and a vanadium catalyst. For example, meta-phenoxybenzoic acid can be effectively converted to meta-phenoxybenzaldehyde in a vapor phase process using hydrogen as the carrier gas/reductant and a catalyst composed at least initially of vanadium pentoxide, either supported or unsupported.

21 Claims, No Drawings

PROCESS FOR CATALYTIC REDUCTION OF CARBOXYLIC ACIDS TO ALDEHYDES

FIELD

This invention relates to a process for the catalytic reduction of a monocarboxylic acid or ester thereof to the corresponding aldehyde in the presence of hydrogen.

BACKGROUND

In the reduction of carboxylic acids and esters to aldehydes, some of the known processes and catalysts are as follows:

Strojny, U.S. Pat. No. 4,328,373, describes the reduction of carboxylic acids or esters to aldehydes using catalysts comprised of oxides of yttrium, cerium, praseodymium, zirconium, thorium, uranium, the lanthanides and actinides or mixtures thereof.

U.S. Pat. No. 4,613,700, Maki et al, reports the catalytic hydrogenation of aromatic carboxylic acids to aldehydes using a zirconium oxide catalyst mixed with manganese, bismuth, chromium, cobalt, iron, zinc, lead, rhenium, indium or elements of Group III in periods 3 to 6 of the periodic chart, as well as lanthanoids such as lanthanum, cerium, praseodymium, neodymium, etc.

U.S. Pat. No. 3,517,066, Gurien et al teaches an improved Rosenmund process for reducing a carbonyl chloride to an aldehyde using a metal catalyst comprised of palladium, osmium, platinum, nickel and a salt of a weak acid and a strong base.

Gelbein et al, U.S. Pat. No. 4,585,899, shows a process for hydrogenation of an aromatic or aliphatic carboxylic acid or ester thereof to the corresponding aldehyde in the presence of a manganese dioxide catalyst supported on activated alumina.

Holy et al, U.S. Pat. No. 4,585,900, teaches a process for hydrogenation of an aromatic or aliphatic carboxylic acid or ester to the corresponding aldehyde using a yttrium catalyst activated with copper.

THE INVENTION

In addition to the above mentioned techniques, it has now been discovered that a vanadium catalyst can be used to reduce monocarboxylic acids or esters to the corresponding aldehydes. Prior to this discovery, vanadium based catalysts were used primarily as oxidation catalysts. Hence it is surprising that reduction of a carboxylic acid can be achieved using the process of this invention.

As disclosed herein, the process of this invention involves contacting the monocarboxylic acid or ester thereof and hydrogen with a vanadium catalyst for a period of time at elevated temperatures such that the acid is reduced to the aldehyde. Using this invention, monocarboxylic acids containing at least 7 carbon atoms up to about 22 carbon atoms can be reduced to the corresponding aldehydes. A preferred class of monocarboxylic acids are those which have a significant vapor pressure below about 500° C. Most preferably acids chosen for the process of this invention have significant vapor pressures below about 350° C. By "significant vapor pressure" is meant a vapor pressure of about 200 to 300 mm Hg at a temperature of about 300° C.

In accordance with this invention, this process may be used for reducing aliphatic and aromatic substituted and unsubstituted monocarboxylic acids or esters thereof. For example, aliphatic monocarboxylic acids that may be used as reactants include such acids as heptanoic, caprylic, nonanoic, capric, lauric, myristic, palmitic, stearic, oleic, linoleic, linolenic, and cyclohexanecarboxylic. Aromatic monocarboxylic acids that may be used as reactants include such acids as phenylacetic; benzoic; o-, m-, or p-toluic; o-, m-, or p-chlorobenzoic; o-, m-, or p-bromobenzoic; o-, m-, or p-nitrobenzoic; salicylic; p-hydroxybenzoic; anthranilic; m-, or p-aminobenzoic; o-, m-, or p-methoxybenzoic; naphthoic; o-, m-, or p-phenoxybenxoic. In a preferred embodiment of this invention, m-phenoxybenzoic acid (MPBAC) is reduced to m-phenoxybenzaldehyde (MPBAD). Other products of the reaction include but are not limited to diphenyl ether (Ph2O), m-phenoxytoluene (MPT), and m-phenoxybenzyl alcohol (MPBA). Those skilled in the art should be able to apply the process taught in this invention to any carboxylic acids or esters containing 7 or more carbon atoms which lend themselves either to vaporization at a temperature of at least 200° C. or that can be dissolved in a suitable solvent and fed into the reactor with a carrier gas.

In the practice of this invention, when an ester is employed as a reactant, the alcohol moiety is preferably derived from a primary alcohol containing from 1 to about 14 carbon atoms. Hence the alcohol moiety may be derived from such alcohols as methyl, ethyl, n-propyl, isopropyl, n-butyl, isobutyl, n-pentyl, isopentyl, n-hexyl, n-heptyl, n-octyl, n-nonyl, n-decyl, lauryl, myristyl, cetyl, allyl, crotyl, benzyl, β-phenylethyl, and cinnamyl. In general the esters of this invention may be represented by the general formula

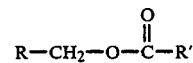

where R represents hydrogen or an aliphatic or aromatic radical containing from 1 to about 13 carbon atoms and R' represents a hydrocarbyl group such as alkyl, aryl, aralkyl, cycloalkyl, alkoxy, alkoxy aryl, aryloxy aryl, and the like containing from about 6 to about 22 carbon atoms.

Of the vanadium catalysts which may be used in the process of this invention, the various vanadium oxides such as vanadium oxide, vanadium dioxide, vanadium trioxide, vanadium tetroxide, vanadium pentoxide, and the various sulfides, such as vanadium sulfide, vanadium disulfide, vanadium trisulfide, and vanadium pentasulfide are preferred. However, other vanadium catalysts may be found to be useful in the invention. Of the preferred catalysts, the vanadium oxide catalysts are the more preferred, with vanadium pentoxide being the most preferred catalyst with which to charge the reactor system. It is believed, however, that as the reaction progresses, vanadium pentoxide is reduced in whole or in part to one or more of the lower oxide forms. Hence, one or more of the lower oxide forms of the vanadium oxide catalyst may be charged ab initio.

The vanadium catalysts employed in the process of this invention may be supported or unsupported. Materials used as support materials include, carbon, pumice, clay, silica, and the oxides of metals including titanium, aluminum, iron, manganese, zirconium, chromium, lead, cobalt, etc. Most preferably the metal oxides used as support for the vanadium oxide catalyst include, titanium dioxide and aluminum oxide. When a supported vanadium pentoxide catalyst is used, the weight percent of vanadium pentoxide catalyst is preferably at least 1% to about 50% of the total supported catalyst, most preferably the vanadium pentoxide will be about 10% by weight of the supported catalyst, the balance being about 90% by weight titanium dioxide or aluminum oxide.

Mixed oxide catalysts containing vanadium may also be used. One such mixed oxide found useful is vanadium pentoxide mixed with stannic oxide. Preferably at least 60% to about 99% of the catalyst weight is vanadium pentoxide, and most preferably, vanadium pentoxide is about 85% by weight of the catalyst, the balance being about 15% by weight stannic oxide. A mixed vanadium pentoxide/stannic oxide catalyst which is supported on carbon, pumice, clay, silica, and the oxides of metals including titanium, aluminum, iron, manganese, zirconium, chromium, lead, cobalt, etc. may also be used for this process.

In the practice of this invention, the catalyst may be pretreated prior to contacting the reagents with the catalyst. This pretreatment of the catalyst is desirable when employing a vanadium oxide catalyst in the process of this invention. In order to accomplish the pretreatment, the catalyst is subjected to a flow of hydrogen for up to 6 or more hours at elevated temperatures normally in the range of about 250° to about 450° C., preferably at least about 300° C. It is believed that the pretreatment results in a reduction of some or all of the vanadium oxide catalyst to a lower oxide form. However, it is not deemed necessary to pretreat the catalyst since it is believed that reduction of the catalyst also results as the reaction progresses. In a particularly preferred embodiment of the invention, the catalyst is pretreated in situ for 2-6 hours at about 350° C. to 400° C. prior to introduction of the reagents to the reactor system.

It is desirable to carry out the process of the present invention at elevated temperatures, of at least 200° C. or higher, preferably 300° C. or higher. More preferably, the process of the present invention is carried out at a temperature in the range of about 325° C. to 450° C. as illustrated in the ensuing examples. While temperatures higher than 450° C. may be used, at highly elevated temperatures there is an increased tendency for the formation of products other than the desired aldehydes. In the case of aromatic acids such as MPBAC, the most preferred temperature is in the range of 325° to 350° C. At temperatures below about 250° C., conversion of MPBAC to MPBAD may be lower than desired. At a temperature above about 450° C., more ethers and fully reduced products are sometimes obtained.

The process of the present invention can be carried out in a batch or a continuous reactor system. The catalyst is placed into a suitable reactor constructed from materials known to be stable at the reaction conditions. One of the by-products of the reaction is water. Therefore, if a halo substituted monocarboxylic acid or ester is used as a reactant, materials suitable to withstand the attack of halo-acids should be chosen. Those skilled in the art should be well acquainted with corrosion protection of reactor systems.

Pressure may be varied over wide limits. The process of the reaction proceeds at subatmospheric as well as superatmospheric pressures. However operation at extremely low or highly elevated pressures is costly and thus less desirable. Preferably, the reaction is conducted at atmospheric or slightly above atmospheric pressure, most preferably at pressures in the range of about 1 to about 2 atmospheres.

The amount of hydrogen used is not critical to the process of this invention however it is preferably added in stoichiometric excess. The molar ratio of hydrogen to carboxylic acid may be from about 1.1:1 to about 30:1 or higher. In a preferred embodiment of this invention hydrogen is not only one of the reactants, it is also used as a carrier gas for the acid or ester reactant.

When hydrogen is used as a carrier gas for the reactants, it is desirable to have a hydrogen flow above about 500 GHSV (gas hourly space velocity) per hour. More preferably, the hydrogen flow is in the range of 600 to about 1500 GHSV per hour, and most preferably in the range of 650 to about 750 GHSV per hour. The acid or ester feed is preferably above at least 0.04 LHSV (Liquid hourly space velocity) per hour and more preferably in the range of 0.05 to 0.20 LHSV per hour, and most preferably in the range of 0.05 to 0.10 LHSV per hour.

The acid or ester may be vaporized and added to the hydrogen stream which is fed into the reactor or may be dissolved in an appropriate solvent and fed into the hydrogen stream. Solvents which may be used in this process should be inert at the reaction conditions such as water, xylene, toluene, benzene, and ethers such as diethyl ether, n-butyl ether, n-propyl ether, isopropyl ether, di-n-butyl ether, diglyme, triglyme, tetraglyme, tetrahydrofuran, anisole, and phenetole. However, other organic solvents may be used, the limits being the solubility of the acid or ester and the possibility of reduction of the solvent at the reaction conditions. In a preferred embodiment of the invention, triglyme is used in the reduction of MPBAC to MPBAD.

Although the process can be carried out in the liquid phase, it is preferable to conduct the process of this invention in the vapor phase using a fixed-bed or a moving or fluidized bed of catalyst.

In the following examples, use was made of a tubular reactor positioned within an Ohio Thermal wire wound tubular furnace, model T11C-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor itself was a 19 inch long, 1 inch diameter stainless steel tube fitted with an internal thermocouple well. The reactor tube was fitted for supply of hydrogen gas from one line and a second line connected to a Milton Roy pump. The second line fed reactants from a reservoir attached thereto. A water condenser below the reactor tube and an ice bath were used to collect liquid in glassware in the ice bath. The vapors transmitted from the glassware in the ice bath were directed to a dry ice bath.

The following procedure was used for all of the runs shown in the Table. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to good standard laboratory practice. The ice water bath and dry ice bath were attached, and the reactor was flushed with hydrogen at the rate of 20–30 cc per minute during furnace warmup and stabilization. To start the run, the hydrogen flow was adjusted to the desired value and fed into the reactor for 1 to 10 hours at about 350°-400° C. to pre-reduce the catalyst. MPBAC dissolved in triglyme was fed in at the desired rate using the Milton Roy pump. Hydrogen was metered in using a standard rotometer. At the end of the run, the furnace was turned off and the column was again purged to remove any remaining hydrogen and reactants.

Examples 1 and 2 illustrate the preparation of typical catalysts for use in the process of this invention.

EXAMPLE 1

$V_2O_5/SnO_2$ Catalyst Preparation

A solution was prepared by dissolving 11.4 grams of $SnCl_4$ plus 3 mL concentrated HCl in 100 mL distilled water which was subsequently neutralized to pH 7 with 14% $NH_4OH$ to precipitate $Sn(OH)_2$. The $Sn(OH)_2$ was filtered and washed free of chloride ion with distilled water. The $Sn(OH)_2$ precipitate was added to an aqueous mixture of 70.3 grams $NH_4VO_3$ and 48.8 grams oxalic acid in 300 mL water. To this mixture was added 14% $NH_4OH$ to pH 10. The dark black precipitate was filtered and washed with distilled water. The gel was extruded through a 50 cc plastic syringe, air-dried, oven-dried at 100° C. for 2 hours then calcined at 450° C. overnight to give 46.2 grams finished catalyst. Its composition was 85.8 weight percent $V_2O_5$ and 14.2 weight percent $SnO_2$.

EXAMPLE 2

$V_2O_5/TiO_2$ Catalyst Preparation

The titanium dioxide supported catalyst can be prepared using the following process. 6.44 grams of $NH_4VO_3$ is added to 100 milliliters of distilled water at 95° C. The solution is decanted onto 45 grams of titanium dioxide which was then oven-dried at 110° C. The remaining $NH_4VO_3$ was dissolved in 75 milliliters of boiling, distilled water and added to the dried previously impregnated $TiO_2$. The impregnated titanium dioxide is then oven-dried at 110° C. overnight then calcined at 600° to 650° C. for 30 minutes then at 450° C. for 6 hours. The resulting catalyst has about 10% vanadium pentoxide supported on titanium dioxide.

Examples 3 through 8, illustrate the process of this invention for the reduction of monocarboxylic acids to the corresponding aldehydes using the apparatus and procedure described above. In each of the examples, the reactor was filled with 20 mL of catalyst. In Examples 3 through 6, MPBAC was reacted in the vapor phase over the indicated catalysts at various temperatures as shown in the Table.

EXAMPLES 3–6 m-Phenoxybenzoic acid reduction m-Phenoxybenzoic acid (MPBAC) was reduced over various catalysts by first dissolving MPBAC in triglyme such that a 15% by weight solution was obtained. The temperature and hydrogen flow rates and other parameters are illustrated by the following Table. Example 3 utilized a 10 wt % vanadium pentoxide catalyst supported on aluminum oxide. Example 4 utilized an unsupported vanadium pentoxide catalyst. Example 5 used a 10 wt % vanadium pentoxide catalyst supported on titanium dioxide. And Example 6 was a mixed catalyst of 85.8 wt % vanadium pentoxide and 14.2 wt % stannic oxide.

TABLE

MPAC Reduction over $V_2O_5$ Catalysts

| Example | Catalysts | Temp, °C. | Acid LHSV,/hr | $H_2$ GHSV,/hr | MPBAC[1] Conv, % | GC %[6] Selectivity $Ph_2O$[2] | MPT[3] | MPBAD[4] | MPBA[5] | Other |
|---|---|---|---|---|---|---|---|---|---|---|
| 3 | $V_2O_5/Al_2O_3$ | 400 | 0.050 | 650 | 9.2 | 18.7 | — | 64.8 | 11.7 | 4.8 |
| | | 425 | 0.054 | 660 | 52.2 | 5.5 | 8.9 | 82.6 | 1.7 | 1.3 |
| | | 450 | 0.050 | 695 | 97.8 | 5.4 | 30.3 | 62.2 | 0.8 | 1.3 |
| | | 420 | 0.050 | 310 | 29.3 | 7.4 | 9.9 | 77.1 | 2.7 | 2.9 |
| 4 | $V_2O_5$ | 350 | 0.050 | 615 | 7.0 | 4.8 | — | 51.2 | 40.8 | — |
| | | 400 | 0.050 | 705 | 75.8 | 3.4 | 64.5 | 3.5 | 2.9 | 25.7 |
| | | 375 | 0.050 | 700 | 100.0 | 0.9 | 88.2 | 5.8 | — | 5.1 |
| | | 350 | 0.050 | 675 | 80.2 | 0.3 | 20.5 | 76.4 | 2.8 | — |
| | | 350 | 0.050 | 660 | 13.2 | — | — | 84.7 | 15.3 | — |
| | | 375 | 0.049 | 660 | 76.2 | 1.5 | 14.5 | 75.9 | 5.7 | 2.3 |
| | | 375 | 0.050 | 695 | 99.7 | 0.4 | 90.4 | 3.1 | — | 6.1 |
| | | 350 | 0.050 | 695 | 95.2 | — | 27.4 | 70.9 | 1.4 | 0.3 |
| | | 340 | 0.050 | 720 | 74.3 | — | 17.4 | 81.1 | 1.5 | — |
| | | 325 | 0.050 | 720 | 43.9 | — | 12.9 | 85.9 | 1.2 | — |
| | | 310 | 0.050 | 715 | 18.6 | — | 9.7 | 88.6 | 1.7 | — |
| | | 325 | 0.050 | 375 | 30.0 | — | 13.5 | 83.5 | 3.0 | — |
| | | 350 | 0.130 | 685 | 25.9 | — | 12.3 | 84.3 | 3.4 | — |
| | | 350 | 0.110 | 790 | 37.4 | — | 13.4 | 84.0 | 2.6 | — |
| | | 350 | 0.068 | 710 | 71.0 | — | 16.6 | 81.5 | 1.9 | — |
| | | 350 | 0.050 | 1220 | 97.8 | — | 44.1 | 55.3 | 0.7 | — |
| 5 | $V_2O_5/TiO_2$ | 350 | 0.050 | 635 | 91.0 | 0.5 | 6.2 | 32.8 | 53.5 | 7.1 |
| | | 325 | 0.050 | 685 | 39.9 | — | 0.4 | 39.0 | 55.7 | 4.9 |
| | | 350 | 0.050 | 630 | 74.4 | 0.7 | 3.3 | 42.1 | 50.6 | 3.4 |
| | | 350 | 0.050 | 1455 | 71.6 | 0.4 | 3.0 | 60.0 | 34.4 | 2.2 |
| | | 350 | 0.100 | 1100 | 32.7 | — | — | 44.3 | 53.5 | 2.2 |
| | | 350 | 0.050 | 985 | 72.5 | 0.7 | 2.7 | 54.8 | 39.5 | 2.2 |
| | | 350 | 0.050 | 1415 | 63.3 | 0.6 | 2.1 | 60.8 | 34.3 | 2.2 |
| | | 350 | 0.034 | 1210 | 85.0 | 0.8 | 4.0 | 65.9 | 26.8 | 2.4 |
| 6 | $V_2O_5/SnO_2$ | 310 | 0.050 | 635 | 37.8 | 3.0 | 10.8 | 53.9 | — | 32.4 |
| | | 310 | 0.050 | 370 | 53.7 | 7.5 | 17.7 | 43.9 | — | 26.7 |
| | | 325 | 0.050 | 650 | 54.4 | 3.9 | 17.5 | 59.9 | — | 19.0 |

TABLE-continued

MPAC Reduction over $V_2O_5$ Catalysts

| Example | Catalysts | Temp, °C. | Acid LHSV,/hr | $H_2$ GHSV,/hr | MPBAC[1] Conv, % | GC %[6] Selectivity | | | | |
|---|---|---|---|---|---|---|---|---|---|---|
| | | | | | | $Ph_2O$[2] | MPT[3] | MPBAD[4] | MPBA[5] | Other |
| | | 350 | 0.050 | 620 | 91.2 | 5.1 | 91.5 | 3.4 | — | — |

[1] MPBAC - m-phenoxybenzoic acid
[2] $Ph_2O$ - diphenyl ether
[3] MPT - m-phenoxytoluene
[4] MPBAD - m-phenoxybenzaldehyde
[5] MPBA - m-phenoxybenzyl alcohol
[6] GC % - gas chromatograph percent distribution of products Examples 7 and 8, illustrate the process of this invention for the reduction of other monocarboxylic acids to the corresponding aldehydes. In these examples, a 10 wt % vanadium pentoxide catalyst supported on titanium dioxide was used.

EXAMPLE 7

Reduction of naphthoic acid to naphthaldehyde

The reactant was 20 wt % naphthoic acid dissolved in triglyme. The acid feed was 0.07 LHSV per hour and the hydrogen flow rate was 650 GHSV per hour. At 350° C. 41% of the naphthoic acid was reduced to the naphthaldehyde with 80% selectivity to the aldehyde and 17% selectivity to methyl naphthoate. At 365° C. conversion of the acid was 37% with 75% selectivity to the naphthaldehyde and 21% selectivity to methyl naphthoate.

EXAMPLE 8

Reduction of nonanoic acid to nonanal

The reactant was 26 wt % nonanoic acid in triglyme fed at the rate of 0.08 LHSV per hour and a hydrogen flow of 650 GHSV per hour. At 350° C. 20% of the nonanoic acid was converted with a 92% selectivity to nonanal and 8% selectivity to 9-heptadecanone. At 375° C., 51% of the acid was converted with an 83% selectivity to nonanal and 15% selectivity to 9-heptadecanone.

Suitability of any given vanadium catalyst in reducing a monocarboxylic acid or ester to an aldehyde can be readily determined by performing a few simple tests in the manner disclosed herein. It must be recognized however, that conditions used in the process of this invention are susceptible to considerable variation as shown in the Table and Examples 3 through 8. It is also possible to vary other aspects of the above described invention without departing from the true spirit and scope thereof.

I claim:

1. A process which comprises reducing at an elevated temperature a monocarboxylic acid containing at least 7 to about 22 carbon atoms, or ester thereof, to an aldehyde in the presence of hydrogen and a vanadium catalyst such that said carboxylic acid or ester is reduced to the corresponding aldehyde, said vanadium catalyst comprising one or more vanadium catalysts selected from a group consisting of vanadium catalysts selected from a group consisting of vanadium oxides and vanadium sulfides.

2. A process of claim 1 wherein the vanadium catalyst is, at least initially, vanadium oxide catalyst.

3. A process of claim 2 wherein the initial vanadium oxide catalyst is pretreated with hydrogen at an elevated temperature, prior to contacting the reagents with the catalyst.

4. A process of claim 2 wherein the vanadium oxide catalyst is pretreated with hydrogen at about 350° to about 400° C. for 2 to 6 hours prior to contacting the reagents with the catalyst.

5. A process of claim 2 wherein the vanadium oxide catalyst initially is vanadium pentoxide.

6. A process of claim 1 wherein the vanadium catalyst is supported on a catalyst support.

7. A process of claim 6 wherein the catalyst support is titanium dioxide, or aluminum oxide.

8. A process of claim 2 wherein the vanadium catalyst is a mixed catalyst with stannic oxide.

9. A process of claim 1 wherein the reduction is conducted in the vapor phase by contacting a vapor phase mixture of the carboxylic acid or ester thereof and hydrogen with the catalyst.

10. A process of claim 1 wherein the reduction is performed at a temperature of about 300° C.

11. A process of claim 5 wherein the catalyst is initially about 10% by weight vanadium pentoxide and about 90% by weight titanium dioxide.

12. A process of claim 5 wherein the vanadium pentoxide catalyst is initially about 10% by weight vanadium pentoxide and about 90% by weight aluminum oxide.

13. A process of claim 8 wherein the catalyst is initially about 85% by weight vanadium pentoxide and about 15% by weight stannic oxide.

14. A process of claim 1 wherein the monocarboxylic acid used is m-phenoxybenzoic acid.

15. A process which comprises reducing m-phenoxybenzoic acid to m-phenoxybenzaldehyde in the presence of hydrogen and a catalyst composed at least initially of vanadium pentoxide such that the m-phenoxybenzoic acid is reduced to m-phenoxybenzaldehyde at a temperature of at least about 300° C., said process being carried out in the vapor phase.

16. A process of claim 15 wherein the catalyst is supported on titanium dioxide or aluminum oxide.

17. A process of claim 15 wherein the catalyst is initially about 10% by weight vanadium pentoxide and about 90% by weight titanium dioxide.

18. A process of claim 15 wherein the catalyst is initially about 10% by weight vanadium pentoxide and about 90% by weight aluminum oxide.

19. A process of claim 15 wherein the catalyst is initially composed of a mixture of vanadium pentoxide and stannic oxide.

20. A process of claim 15 wherein the initial vanadium pentoxide catalyst is pretreated with hydrogen at an elevated temperature prior to contacting the reagents with the catalyst.

21. A process of claim 15 wherein the vanadium pentoxide catalyst is pretreated with hydrogen at about 350° to about 400° C. for 2 to 6 hours prior to contacting the reagents with the catalyst.

* * * * *